US012749154B2

(12) United States Patent
Gurevich

(10) Patent No.: US 12,749,154 B2
(45) Date of Patent: Sep. 29, 2026

(54) SYSTEM AND METHOD FOR ENHANCING MEDICAL IMAGES, GENERATING REFLECTANCE IMAGE FROM BRIGHTNESS COMPONENT IMAGE USING MACHINE LEARNING MODEL

(71) Applicant: Stryker Corporation, Kalamazoo, MI (US)

(72) Inventor: Lina Gurevich, Vancouver (CA)

(73) Assignee: Stryker Corporation, Portage, MI (US)

( * ) Notice: Subject to any disclaimer, the term of this patent is extended or adjusted under 35 U.S.C. 154(b) by 246 days.

(21) Appl. No.: 18/539,098

(22) Filed: Dec. 13, 2023

(65) Prior Publication Data

US 2024/0212104 A1 Jun. 27, 2024

Related U.S. Application Data

(60) Provisional application No. 63/476,636, filed on Dec. 21, 2022.

(51) Int. Cl.

*G06T 5/50* (2006.01)
*G06T 5/60* (2024.01)
*G06T 5/70* (2024.01)
*G16H 15/00* (2018.01)
*G16H 30/40* (2018.01)
*G06T 7/90* (2017.01)

(Continued)

(52) U.S. Cl.

CPC .................. *G06T 5/50* (2013.01); *G06T 5/60* (2024.01); *G06T 5/70* (2024.01); *G16H 15/00* (2018.01); *G16H 30/40* (2018.01); *G06T 7/90* (2017.01); *G06T 2207/10016* (2013.01); *G06T 2207/10024* (2013.01); *G06T 2207/10064* (2013.01); *G06T 2207/20081* (2013.01); *G06T 2207/20092* (2013.01); *G06T 2207/30004* (2013.01); *H04N 1/46* (2013.01); *H04N 1/60* (2013.01)

(58) Field of Classification Search

None
See application file for complete search history.

(56) References Cited

U.S. PATENT DOCUMENTS 9,135,701 B2 * 9/2015 Guissin .................. A61B 5/444
10,039,439 B2 8/2018 Aoyama
10,997,690 B2 5/2021 Schwartz et al.

(Continued)

FOREIGN PATENT DOCUMENTS

CN 110910317 * 3/2020
CN 112001863 A 11/2020

(Continued)

OTHER PUBLICATIONS

Machine Translation of CN Pub 110910317 (in English from Chinese) to Guo et al.*

(Continued)

*Primary Examiner* — Haris Sabah
(74) *Attorney, Agent, or Firm* — Morrison & Foerster LLP

(57) ABSTRACT

A method of enhancing medical images includes, at a computing system: receiving a medical image; converting the medical image into a brightness component image and two color component images; generating a reflectance image from the brightness component image using a machine learning model; and generating an enhanced medical image based on the reflectance image.

34 Claims, 9 Drawing Sheets

(51) Int. Cl.

*H04N 1/46* (2006.01)
*H04N 1/60* (2006.01)

(56) References Cited

U.S. PATENT DOCUMENTS

| | | | | |
|---|---|---|---|---|
| 2008/0226148 | A1* | 9/2008 | Gu | G06T 5/90 382/128 |
| 2010/0185064 | A1* | 7/2010 | Bandic | A61B 5/444 600/306 |
| 2012/0127200 | A1* | 5/2012 | Kohara | G06T 15/08 345/629 |
| 2012/0200694 | A1* | 8/2012 | Garsha | G01N 21/6456 382/128 |
| 2016/0171718 | A1* | 6/2016 | Kuramoto | A61B 5/0084 382/128 |
| 2021/0133932 | A1 | 5/2021 | Lee et al. | |
| 2021/0169306 | A1 | 6/2021 | Oosake | |
| 2021/0192727 | A1* | 6/2021 | Ward | G06T 11/20 |
| 2021/0306558 | A1 | 9/2021 | Feng et al. | |
| 2021/0390340 | A1 | 12/2021 | Zhang | |
| 2021/0397865 | A1 | 12/2021 | Juergens | |
| 2022/0039743 | A1 | 2/2022 | Meguro | |
| 2022/0211258 | A1* | 7/2022 | Westwick | A61B 1/0005 |
| 2022/0375047 | A1 | 11/2022 | Gurevich | |

FOREIGN PATENT DOCUMENTS

| | | | |
|---|---|---|---|
| CN | 112614077 | A | 4/2021 |
| CN | 112801898 | A | 5/2021 |
| CN | 112927160 | A | 6/2021 |
| CN | 113096023 | A | 7/2021 |
| CN | 113256510 | A | 8/2021 |
| CN | 113344804 | A | 9/2021 |
| CN | 113313657 | B | 12/2021 |
| CN | 113496489 | B | 12/2021 |
| CN | 114119422 | A | 3/2022 |
| WO | 2021/046752 | A1 | 3/2021 |

OTHER PUBLICATIONS

International Preliminary Report on Patentability dated Jun. 24, 2025, directed to International Application No. PCT/US2023/083830; 6 pages.

International Search Report and Written Opinion mailed Mar. 18, 2024, directed to International Application No. PCT/US2023/083830; 10 pages.

Jiang et al. (2021). "EnlightenGAN: Deep Light Enhancement Without Paired Supervision," IEEE Transactions on Image Processing 30: 2340-2349.

Jiang et al. (Jan. 3, 2021). "A Switched View of Retinex: Deep Self-Regularized Low-Light Image Enhancement," located at https://doi.org/10.48550/arXiv.2101.00603, 9 pages.

Li et al. (Mar. 1, 2021). "Learning to Enhance Low-Light Image via Zero-Reference Deep Curve Estimation," located at https://arxiv.org/abs/2103.00860, 14 pages.

Liang et al. (Jul. 4, 2020). "Deep Bilateral Retinex for Low-Light Image Enhancement," located at https://arxiv.org/abs/2007.02018, 16 pages.

Lu et al. (2021). "TBEFN: A Two-Branch Exposure-Fusion Network for Low-Light Image Enhancement," IEEE Transactions on Multimedia 23: 4093-4105.

Park et al. (2018). "Dual Autoencoder Network for Retinex-Based Low-Light Image Enhancement," IEEE Access 6: 22084-22093.

Wikipedia. (Aug. 9, 2024). "Color constancy," located at https://en.wikipedia.org/wiki/Color_constancy, 10 pages.

Zhang et al. (Mar. 1, 2021). "Self-supervised Low Light Image Enhancement and Denoising," located at https://doi.org/10.48550/arXiv.2103.00832, 10 pages.

Zhong et al. "Feature Based Deep Retinex for Low-Light Image Enhancement," 19th Brazilian Symposium on Software Quality, Nov. 13, 2020, São Luís, Brazil; pp. 66-71.

* cited by examiner

SYSTEM AND METHOD FOR ENHANCING MEDICAL IMAGES, GENERATING REFLECTANCE IMAGE FROM BRIGHTNESS COMPONENT IMAGE USING MACHINE LEARNING MODEL

CROSS-REFERENCE TO RELATED APPLICATIONS

This application claims the benefit of U.S. Provisional Application No. 63/476,636, filed Dec. 21, 2022, the entire contents of which are hereby incorporated by reference herein.

FIELD

The present disclosure is related generally to medical imaging, and more specifically, to image processing for medical imaging.

BACKGROUND

Minimally invasive surgery generally involves the use of a high-definition camera coupled to an endoscope inserted through a small incision into a patient to provide a surgeon with a clear and precise view within the body with minimal tissue damage. The endoscope emits light from its distal end to illuminate the surgical cavity and receives light reflected or emitted by tissue within the surgical cavity through a lens or window located at the distal end of the endoscope. Effectively illuminating the surgical cavity for imaging can be challenging. The confined nature of the surgical cavity and the unidirectional illumination provided by the endoscope often leads to inconsistent illumination of the surgical field. For example, regions closer to the distal end of the endoscope may be brightly illuminated while regions further from the distal end may be poorly illuminated. Poor illumination is not limited to endoscopic imaging and can affect many different imaging modalities. For example, an open-field breast reconstruction surgery often relies on near-infrared fluorescence imaging to assess the quality of perfusion and may suffer from low intensity fluorescence excitation illumination. Poor illumination can lead to poor imaging, with detail of poorly illuminated regions being difficult to discern in the resulting imaging. Efforts to increase image brightness for poorly illuminated regions may cause problems for other regions. For example, increasing the level of illumination and/or increasing the camera gain may lead to color distortion (oversaturation) of regions that are more brightly illuminated, rendering images unreliable for abnormality detection and diagnosis in tissue.

SUMMARY

According to an aspect, medical image processing systems and methods enhance low brightness regions in medical images (single images or video frames) by separating the brightness component from color components of the image, generating a reflectance image from the brightness component, and combining the reflectance image and the color components into an enhanced image in which the low brightness regions are enhanced and the color components are reserved. With enhanced brightness and preserved color components, the enhanced image can be used to better analyze imaged tissue.

According to an aspect, a method of enhancing medical images includes, at a computing system: receiving a medical image; converting the medical image into a brightness component image and two color component images; generating a reflectance image from the brightness component image using a machine learning model; and generating an enhanced medical image based on the reflectance image.

The enhanced medical image may include at least one region that is brighter than a corresponding region of the medical image.

The machine learning model may have been trained on training images that comprise non-medical training images. The machine learning model may have been trained on the non-medical training images in a first training stage and trained on medical training images in a second training stage that is subsequent to the first training stage.

Generating the enhanced medical image may include applying at least one de-noising algorithm.

The medical image may include a grayscale image. The grayscale image may include three color components.

The two color component images may be a hue image and a saturation image.

The enhanced medical image may be generated based on the reflectance image and the two color component images.

The medical image may be a fluorescence image and the enhanced medical image may include a combination of a visible light image with the reflectance image.

The medical image may include a fluorescence image and the enhanced medical image may comprise an enhanced fluorescence image. The method may include receiving a visible light image and combining the visible light image with the enhanced fluorescence image.

The method may include displaying the enhanced medical image during a medical procedure.

The method may include generating a medical procedure report that comprises the enhanced medical image.

The method may include displaying the enhanced medical image to a user; receiving at least one input from the user for labeling anatomy of interest in the medical image to generate a training medical image; and training a different machine learning model to identify the anatomy of interest based on the training medical image.

The medical image may be one of a plurality of medical images captured under multiple lighting conditions, and the method may include generating a plurality of enhanced medical images from the plurality of medical images using the machine learning model; and training a different machine learning model based on the plurality of enhanced medical images.

The medical image may include a video frame. The medical image may include an endoscopic image. The medical image may include an open-field image.

The method may include receiving a user input selecting an enhancement mode, and generating the enhanced medical image in response to receiving the user input.

According to an aspect, a computing system includes one or more processors, memory, and one or more programs stored in the memory for execution by the one or more processors, the one or more programs including instructions that, when executed by the one or more processors, cause the computing system to: receive a medical image; convert the medical image into a brightness component image and two color component images; generate a reflectance image from the brightness component image using a machine learning model; and generate an enhanced medical image based on the reflectance image.

The enhanced medical image may include at least one region that is brighter than a corresponding region of the medical image.

The machine learning model may have been trained on training images that comprise non-medical training images. The machine learning model may have been trained on the non-medical training images in a first training stage and trained on medical training images in a second training stage that is subsequent to the first training stage.

Generating the enhanced medical image may include applying at least one de-noising algorithm.

The medical image may include a grayscale image. The grayscale image may include three color components.

The two color component images may be a hue image and a saturation image.

The enhanced medical image may be generated based on the reflectance image and the two color component images.

The medical image may be a fluorescence image and the enhanced medical image may include a combination of a visible light image with the reflectance image.

The medical image may include a fluorescence image and the enhanced medical image may comprise an enhanced fluorescence image. The one or more programs may include instructions for receiving a visible light image and combining the visible light image with the enhanced fluorescence image.

The one or more programs may include instructions for displaying the enhanced medical image during a medical procedure.

The one or more programs may include instructions for generating a medical procedure report that comprises the enhanced medical image.

The one or more programs may include instructions for: displaying the enhanced medical image to a user; receiving at least one input from the user for labeling anatomy of interest in the medical image to generate a training medical image; and training a different machine learning model to identify the anatomy of interest based on the training medical image.

The medical image may be one of a plurality of medical images captured under multiple lighting conditions, and the one or more programs may include instructions for: generating a plurality of enhanced medical images from the plurality of medical images using the machine learning model; and training a different machine learning model based on the plurality of enhanced medical images.

The medical image may include a video frame. The medical image may include an endoscopic image. The medical image may include an open-field image.

The one or more programs may include instructions for receiving a user input selecting an enhancement mode, and generating the enhanced medical image in response to receiving the user input.

According to an aspect, a non-transitory computer readable storage medium storing one or more programs for execution by a computing system to cause the computing system to perform any of the above methods.

According to an aspect, a computer program product comprises software code portions for execution by a computing system to cause the computing system to perform any of the above methods.

The computing systems and methods described herein concern the processing of medical images. The systems and methods receive the medical image(s). The systems and methods may exclude a step of image acquisition. There is no link between the system and methods described herein and the effects produced by the image acquisition assembly on the body. In the instance the image acquisition assembly is an endoscopic camera extending from the endoscope, the endoscope can be pre-inserted into the body. Thus, the method described in greater detail below can exclude the step of inserting the endoscope into the body. The method is not a method of treatment of the body.

It will be appreciated that any of the variations, aspects, features, and options described in view of the systems apply equally to the methods and vice versa. It will also be clear than any one or more of the above variations, aspects, features, and options can be combined.

BRIEF DESCRIPTION OF THE FIGURES

The invention will now be described, by way of example only, with reference to the accompanying drawings, in which.

DETAILED DESCRIPTION

Figure 1:
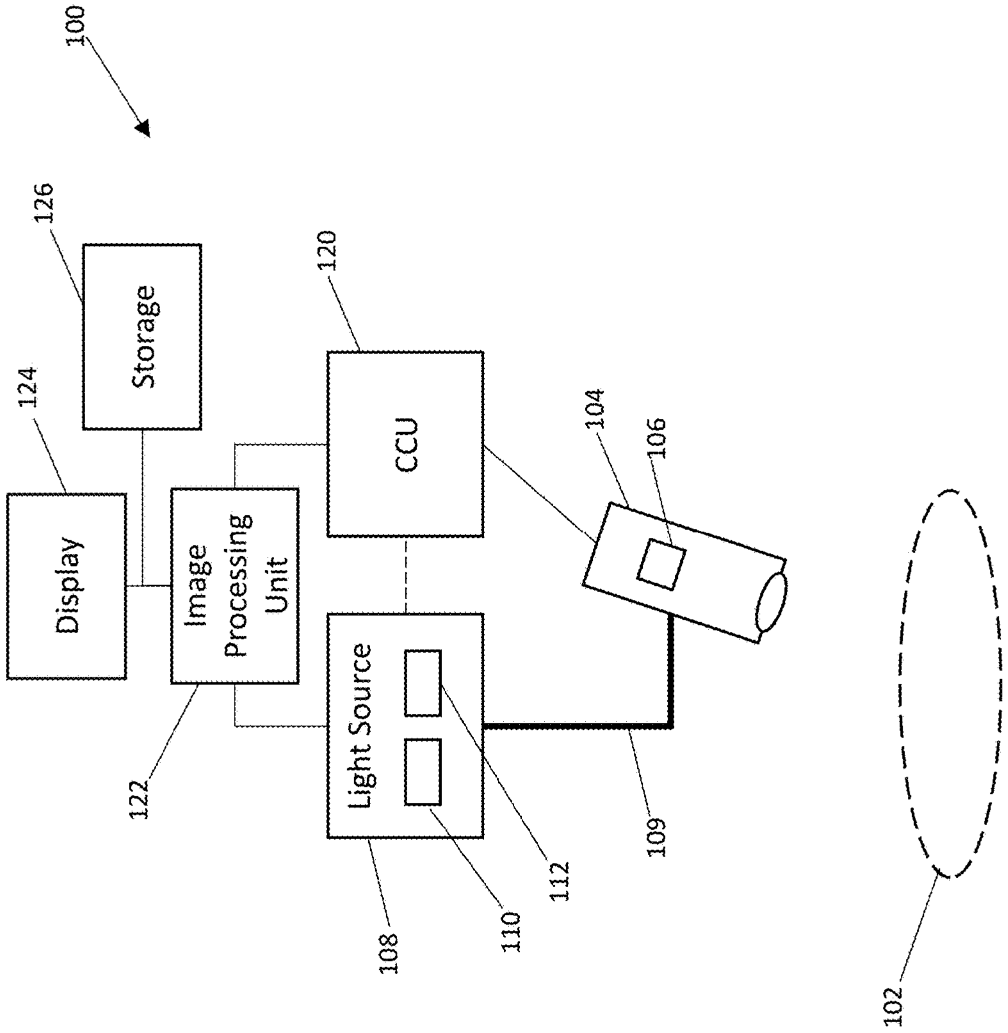
FIG. 1 illustrates a block diagram of an example imaging system.

Reference will now be made in detail to implementations and examples of various aspects and variations of systems and methods described herein. Although several exemplary variations of the systems and methods are described herein, other variations of the systems and methods—may include aspects of the systems and methods described herein combined in any suitable manner having combinations of all or some of the aspects described herein.

According to various aspects, systems and methods can enhance brightness of medical images (single images or video frames) via a process that isolates the brightness component from the color components (e.g., hue and saturation) of a medical image, generates a reflectance image from the brightness component, and combines the reflectance image with the color components to generate an enhanced medical image. This achieves improved brightness of low brightness regions without introducing color distortion (e.g., oversaturation) in the color components of the image. Image brightness is enhanced and color fidelity is preserved. With improved image brightness and preserved color fidelity, the enhanced images can be used to better analyze imaged tissue, such as for improved detection of abnormalities or other aspects of the imaged tissue.

The methods and systems described herein may be used for enhancing images from a variety of imaging modalities, including but not limited to white light imaging, fluorescence imaging, radiation imaging (e.g., x-ray images gathered from imaging procedures such as computed tomography (CT) scans, positron emission tomography (PET) scans, etc.), magnetic resonance imaging (MRI), and/or ultrasound imaging. The medical images may comprise endoscopic images, open-field images, etc. The enhanced images may be generated and displayed real-time during an imaging session to provide enhanced visualization of tissue of interest to a user during the imaging session. The enhanced medical images may be used to provide better data for image processing techniques and/or better training data for training machine learning models, such as for improved image segmentation and/or image classification.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates an example imaging system 100 for imaging tissue 102 of a subject during an imaging session, a surgical procedure, or a non-surgical medical procedure. System 100 includes an image acquisition assembly 104 (also referred to herein as an imager) that has at least one image sensor 106 configured to capture an image or a sequence of images (e.g., video frames) depicting tissue and/or one or more features of the tissue. The image acquisition assembly 104 can be a hand-held device, such as an open-field camera or an endoscopic camera.

The medical procedure in which medical images may be captured using an open-field camera and/or endoscopic camera may be an exploratory procedure, a diagnostic procedure, a study, a surgical procedure, a non-surgical procedure, an invasive procedure, or a non-invasive procedure. It is to be understood that the terms endoscopy and endoscopic are not intended to be limiting, and the imaging system 100 may be configured to capture medical images from various scope-based procedures including but not limited to arthroscopy, ureteroscopy, laparoscopy, colonoscopy, bronchoscopy, etc.

The image acquisition assembly 104 may be connected to a camera control unit (CCU) 120, which may generate one or more single snapshot images and/or video frames (referred to herein collectively as images) from imaging data generated by the image acquisition assembly 104. The images generated by the camera control unit 120 may be transmitted to an image processing unit 122 that may apply one or more image processing techniques described in greater detail below to the images. A computing system may comprise the image processing unit 122. Optionally, the camera control unit 120 and the image processing unit 122 may be integrated into a single device. The image processing unit 122 (and/or the camera control unit 120) may be communicatively coupled (e.g., via wired and/or wireless connection) to one or more displays 124 for displaying the one or more images generated by the camera control unit 120 and/or one or more images or other visualizations generated based on the images generated by the camera control unit 120. The image processing unit 122 (and/or the camera control unit 120) may store the one or more images generated by the camera control unit 120 and/or one or more images or other visualizations generated based on the images generated by the camera control unit 120 in one or more storage devices 126. The one or more storage devices can include one or more local memories, one or more remote memories, a recorder or other data storage device, a printer, and/or a picture archiving and communication system (PACS). The system 100 may additionally or alternatively include any suitable systems for communicating and/or storing images and image-related data.

The medical images generated using camera control unit 120 may be described herein as visible (e.g., white) light images and/or fluorescence images. However, it is to be understood that the imaging system 100 of FIG. 1 may be configured to generate images and/or video frames according to any other suitable imaging modality, including but not limited to radiation imaging (e.g., x-ray images gathered from imaging procedures such as CT scans, PET scans, etc.), MRI, and/or ultrasound imaging. Thus, the image processing unit 122 may be configured to process medical images such as visible light images, fluorescence images, MRI images, ultrasound images, etc.

The imaging system 100 may include a light source 108 configured to generate light that is directed to the field of view to illuminate the tissue 102. Light generated by the light source 108 can be provided to the image acquisition assembly 104 by a light cable 109. The image acquisition assembly 104 may include one or more optical components, such as one or more lenses, fiber optics, light pipes, etc., for directing the light received from the light source 108 to the tissue. As mentioned above, the image acquisition assembly 104 may be an endoscopic camera comprising an endoscope that includes one or more optical components for conveying the light to a scene within a surgical cavity into which the endoscope is inserted. Moreover, the image acquisition assembly 104 may be an open-field imager and may include one or more lenses that direct the light toward the field of view of the open-field imager.

The light source 108 includes one or more visible light emitters 110 that emit visible light in one or more visible wavebands (e.g., full spectrum visible light, narrow band visible light, or other portions of the visible light spectrum). The visible light emitters 110 may include one or more solid state emitters, such as LEDs and/or laser diodes. The visible light emitters 110 may include blue, green, and red (or other color components) LEDs or laser diodes that in combination generate visible light illumination. These color component light emitters may be centered around the same wavelengths around which the image acquisition assembly 104 is centered. For example, in variations in which the image acquisition assembly 104 includes a single chip, single color image sensor having an RGB color filter array deposited on its pixels, the red, green, and blue light sources may be centered around the same wavelengths around which the RGB color filter array is centered. As another example, in variations in which the image acquisition assembly 104 includes a three-chip, three-sensor (RGB) color camera system, the red, green, and blue light sources may be centered around the same wavelengths around which the red, green, and blue image sensors are centered.

The light source 108 can include one or more excitation light emitters 112 configured to emit excitation light suitable for exciting intrinsic fluorophores and/or extrinsic fluorophores (e.g., a fluorescence imaging agent introduced into the object) located in the tissue being imaged. The excitation light emitters 112 may include, for example, one or more LEDs, laser diodes, arc lamps, and/or illuminating technologies of sufficient intensity and appropriate wavelength to excite the fluorophores located in the object being imaged. For example, the excitation light emitter(s) may be configured to emit light in the near-infrared (NIR) waveband (such as, for example, approximately 805 nm light), though other excitation light wavelengths may be appropriate depending on the application.

The light source 108 may further include one or more optical elements that shape and/or guide the light output from the visible light emitters 110 and/or excitation light emitters 112. The optical components may include one or more lenses, mirrors (e.g., dichroic mirrors), light guides and/or diffractive elements, e.g., so as to help ensure a flat field over substantially the entire field of view of the image acquisition assembly 104.

The image acquisition assembly 104 may acquire reflected light images based on visible light that has reflected from the tissue, and/or fluorescence images based on fluorescence emitted by fluorophores in the tissue that are excited by the fluorescence excitation light. The at least one image sensor 106 may include at least one solid state image sensor. The at least one image sensor 106 may include, for example, a charge coupled device (CCD), a CMOS sensor, a CID, or other suitable sensor technology. The at least one image sensor 106 may include a single image sensor (e.g., a grayscale image sensor or a color image sensor having an RGB color filter array deposited on its pixels). The at least one image sensor 106 may include three-sensors, such as one sensor for detecting red light, one for detecting green light, and one for detecting blue light.

The camera control unit 120 can control timing of image acquisition (e.g., frame acquisition rate) by the image acquisition assembly 104. The image acquisition assembly 104 may be used to acquire both visible light images and/or fluorescence images and the camera control unit 120 may control a timing scheme for the image acquisition assembly 104. The camera control unit 120 may be connected to the light source 108 for providing timing commands to the light source 108. Alternatively, the image processing unit 122 may control a timing scheme of the image acquisition assembly 104, the light source 108, or both.

Figure 2:
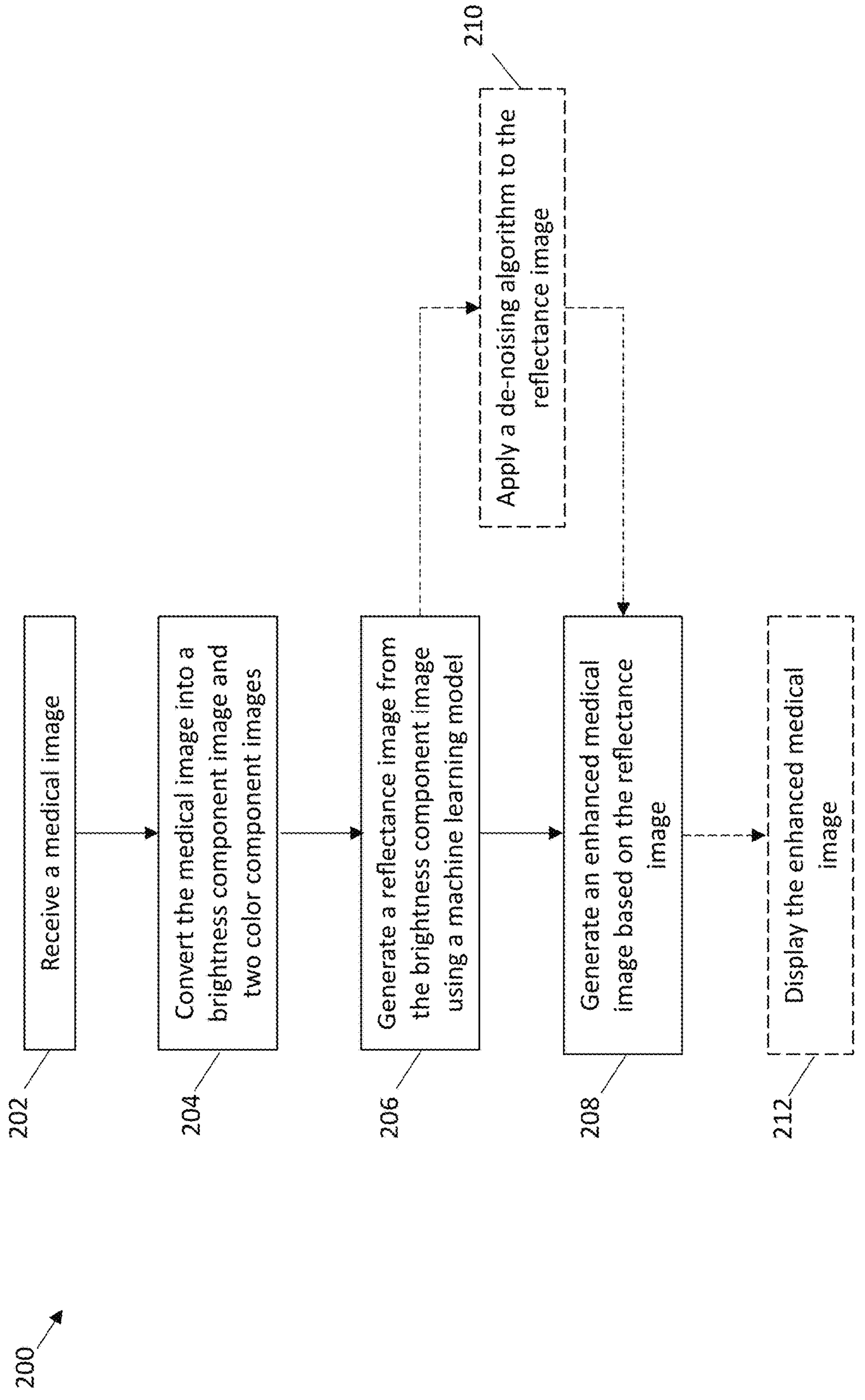
FIG. 2 illustrates an example method for generating an enhanced medical image.

FIG. 2 illustrates an example method 200 for generating an enhanced medical image. The method 200 may be performed by a computing system on one or more images generated by an imaging system, such as imaging system 100 illustrated in FIG. 1 and described above. Method 200 may be performed by imaging system 100 itself. For example, method 200 may be performed by image processing unit 122 described above. At least a portion of method 200 may be performed by a GPU, such that images (and/or video frames) may be enhanced and displayed in real-time.

At step 202, at least one medical image may be received at a computing system. The medical image may be received from an imaging system or a component of an imaging system or may be received from a memory in which a previously generated medical image was be stored. The medical image may be a fluorescence image, visible light (e.g., white light) image, ultrasound image, MRI image, etc. The medical image may be a low-light image, such as a visible light image captured under poor illumination conditions or a low-dose CT scan. The one or more medical images can include a single snapshot image or may be a sequence of images received frame-by-frame in a continuous fashion as the frames are generated (i.e., in real-time). For simplicity, the description below refers to a single medical image but it should be understood that the same steps can be applied to multiples medical images, including a series of frames of a video.

The received medical image may be a color image, such as a white light image, or a grayscale image, such as a fluorescence image or X-ray image. The medical image, whether a color image or a grayscale image, may comprise an array of pixel data having multiple colors, such as an array of RGB (red, green, blue) pixel values (referred to herein as RGB color space). Although RGB color space is mentioned below, it should be understood that the medical image can comprise pixel data of any suitable color space.

At step 204, the medical image may be converted into a brightness component image and color component images. For example, the medical image may be converted from the RGB color space to an HSV (hue, saturation, value) color space, where the brightness component image is the array of "value" values and the color component images are the arrays of hue values and saturation values. The HSV color space is also referred to as an HSB color space (where B corresponds with brightness). It is to be understood that value and brightness are analogous. The image may be converted from RGB color space to HSV color space in any suitable fashion. In some examples, the medical image may be received in a representation already corresponding to the HSV color space. In such cases, no conversion between color models may be necessary, and step 204 in method may be skipped and the method 200 may proceed accordingly to step 206.

At step 206, a reflectance image is generated based on the brightness component image. The brightness component image may be inputted to a reflectance estimation machine learning model, such as a reflectance estimation network illustrated and described in greater detail below with respect to FIG. 3A. The reflectance estimation machine learning model generates a reflectance image that is an estimation of the reflectances of tissue or other features in the image. As is known in the art, reflectance is the ratio of energy reflected to the total energy incident on a body and, as such, is independent of the amount of light incident on the surface. Therefore, the reflectance image includes, for each pixel in the original medical image, an estimate of the proportion of light incidence on a surface that is reflected by that surface at the location corresponding to the pixel.

At step 208, an enhanced medical image may be generated based on the reflectance image. The enhanced medical image may be generated by combining the reflectance image with the hue and saturation component images generated in step 204. Combining the reflectance image with the hue and saturation images may include converting the image from the HSV color space back to the RGB color space. For example, the pixel data for each of the red, green, and blue images may be determined from the hue, saturation, and value images of the HSV color space.

Generating an enhanced medical image may include combining (e.g., overlaying) a visible light image and a fluorescence image of the same scene. For example, a brightness image generated based on the fluorescence image may be passed through the reflectance estimation network to generate a reflectance image, and the reflectance image and the visible light image may be overlaid to generate an enhanced image that is a combined white light and fluorescence image. In another example, the reflectance image generated based on the original fluorescence image may be combined with the color channels of the fluorescence image (the hue image and saturation image) to generate an enhanced fluorescence image, and this enhanced image may be overlaid with a visible light image.

Optionally, prior to generating an enhanced medical image based on the reflectance image, at step 210 of method 200 at least one de-noising algorithm may be applied to the generated reflectance image. For example, the de-noising algorithm may be a variational de-noising algorithm (e.g., non-local means, total variation regularization, sparse representation, low-rank minimization, etc.). Other example de-noising algorithms may include but are not limited to spatial domain filtering, transform domain filtering (e.g., data adaptive transform, non-data adaptive transform, etc.), BM3D, MLP models, and/or deep learning-based methods. In some aspect, the de-noising algorithm may be applied uniformly to the generated reflectance image such that each pixel is evaluated by the algorithm at once. In some aspect, the de-noising algorithm may be applied selectively to each individual pixel of the medical image. For example, each pixel that comprises a threshold level of noise may have the de-noising algorithm applied to it.

Optionally, at step 212, the enhanced medical image may be displayed. The enhanced medical image may be displayed on a display screen during a medical procedure, such as a surgical procedure, non-surgical procedure, imaging session, etc. As mentioned above, the enhanced medical image may be displayed in real-time, such that the enhancement of images may be performed as they are received. For example, the enhanced image may be displayed intra-operatively in the operating room to assist a surgeon in identifying tissue. The enhanced medical images may be observed to detect abnormalities in the imaged tissue and to aid in determining a diagnosis. Example enhanced medical images are provided at least in FIGS. 4A-4D and FIGS. 5A-5D, and are described in greater detail below.

Step 212 may include, additionally or alternatively, using the enhanced medical image or at least a portion thereof for a medical procedure report. For example, the enhanced medical image may be added to a medical procedure report during a medical procedure (automatically or manually) or may be added to a medical procedure report after completion of the medical procedure. Optionally, a non-enhanced medical image is displayed during a medical procedure, and the enhanced medical image is generated after the medical procedure and included in the medical procedure report. The enhanced medical image may be analyzed by a medical practitioner, such as to evaluate a state of tissue in the enhanced medical image and may include an assessment of the tissue in the medical procedure report.

Method 200 may be repeated for each image in a sequence of images (e.g., video frames). For example, a series of images may be generated in real-time during an endoscopic procedure to assist a clinician in visualizing the tissue in the imaging field, and method 200 may be performed on each image as they are generated. In some examples, enhanced images may be generated and displayed as an enhanced video on a display screen to assist the clinician in visualizing the field of view. Additionally or alternatively, enhanced images and video frames can be included in medical procedure reports.

Method 200 can include illuminating the imaging region (e.g., tissue) with an illumination light, capturing the one or more images, and transferring the captured one or more images from the camera to an image processing system for low-light enhancement of the images (e.g., image processing unit 122).

In some examples, images may be analyzed to determine whether low-light image enhancement is needed, such that method 200 may be performed on an ad-hoc basis based on a determination that enhancement is needed. The determination can be made, for example, by image processing unit 122. For example, method 200 may be applied in a predefined pattern to the received images (e.g., each $n^{th}$ image may be processed with system 300, where n may equal 2, 3, 4, 5, etc.). In another example, method 200 may be applied to one or more images which meet or exceed a predefined threshold. For example, the imaging system may be configured to apply the image enhancement process to images with a brightness at or below a predefined threshold. Thus, in each of the aforementioned examples, intermediate images may be skipped, which may improve the speed at which the system may process images. In some examples, a user can command image enhancement, such as by viewing and selecting images that the user considers too dark. Thus, the imaging system may be configured to receive a user input comprising an indication of when to enable and disable the image processing unit. In some examples, method 200 is performed regardless of whether enhancement is subjectively needed, because method 200 does not result in color distortion (e.g., saturation) and therefore poses little risk for image degradation.

Figure 3A:
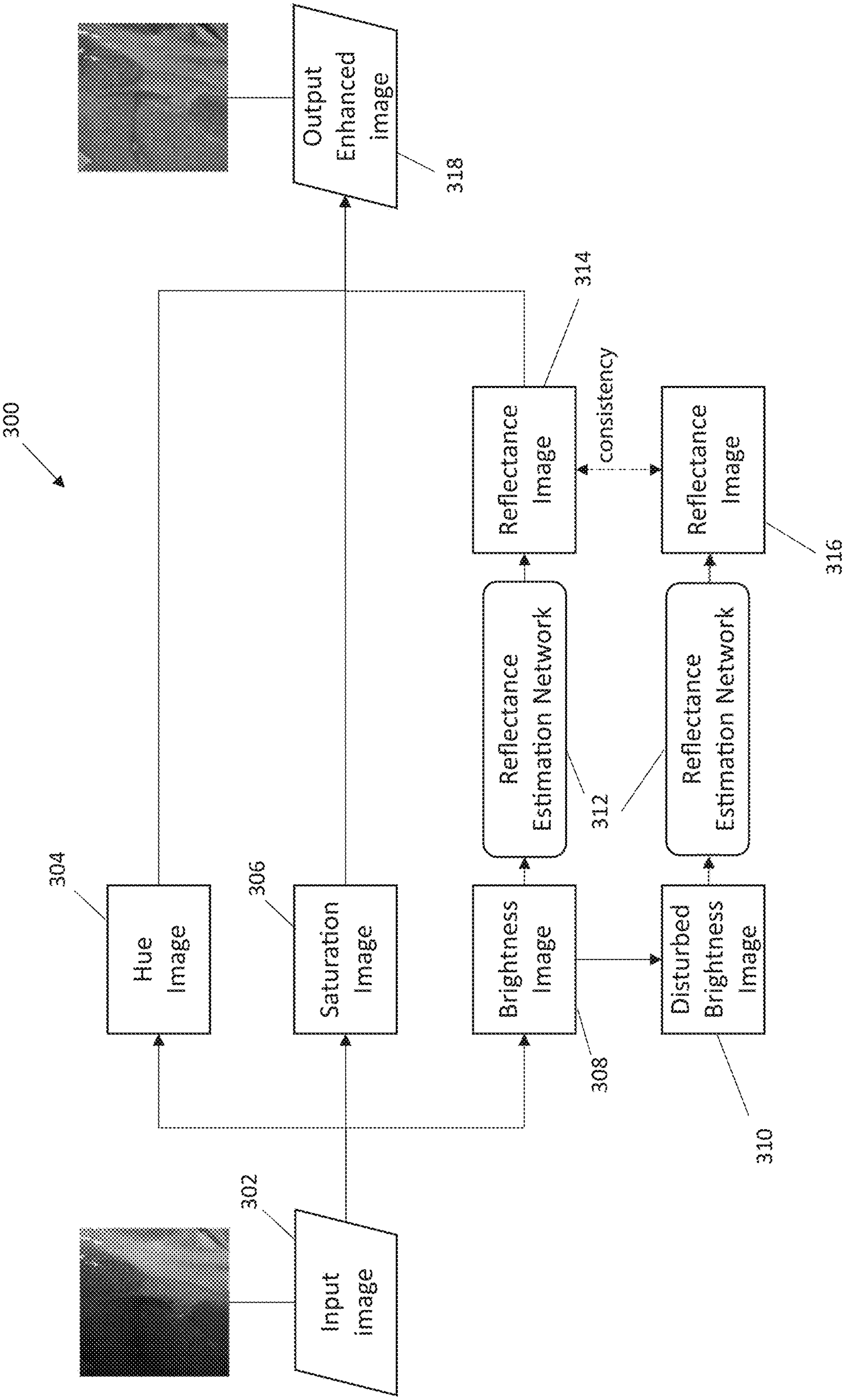
FIG. 3A illustrates an example method for training a machine learning model for generating a reflectance image.

FIG. 3A illustrates an example method 300 for training a machine learning model to generate a reflectance image according to step 206 of method 200. The machine learning model is trained on a set of training images that can include exclusively medical images, exclusively non-medical images, and/or a combination of medical and non-medical images. FIG. 3A represents the set of training images by input image 302, but this is merely for simplicity, and it should be understood that the input image 302 represents a suitable number (e.g., hundreds, thousands) of training images. The input image 302 may be a medical image or non-medical image. The set of training images that includes input image 302 may include non-medical images, medical images, or both.

The input image 302 may be separated into the three channels of the HSV color space in similar fashion to step 204 of method 200. The input image 302 may be separated into a hue channel 304, a saturation channel 306, and a brightness channel 308.

Training the machine learning model (otherwise referred to as a reflectance estimation network) may include generating a disturbed brightness image 310 based on the original brightness image 308 and passing each of the brightness image 308 and disturbed brightness image 310 through the reflectance estimation network 312 to generate a reflectance image 314 and a reflectance image 316, respectively. Each of these steps will be described in greater detail below.

The disturbed brightness image 310 may be obtained using a nonlinear (e.g., power) function with a randomly selected exponent. For example, the power function may be applied to the pixel data corresponding to the brightness image 308. In some aspect, the power function may be monotonically increasing to maintain consistency in the gradient direction between the original brightness image 308 and disturbed brightness image 310. With the use of a random exponent, the diversity in disturbance may be increased. Expression 1 below demonstrates the relationship between the disturbed brightness and original brightness, where V(x) denotes pixel values and gamma (γ) denotes a random value.

$$V'(x) = V(x)^{\gamma} \quad (1)$$

The disturbed brightness may be used to restrict the consistency of reflectance determined from the use of the machine learning model, rather than requiring an extensive training dataset to determine reflectance. In some examples, if the average value of the brightness (V) is less than 0.5, the gamma may be between 0 and 1. If the value of the brightness exceeds 0.5, gamma may be between 1 and 5.

The Retinex theory states that images of the same scene but captured under different lighting conditions share the same reflectance properties. Based on this theory, an image (e.g., brightness image 308 and disturbed brightness image 310) can be decomposed into reflectance and illumination. Under the assumption that illumination is smooth, a reflectance image can be generated using the reflectance estimation network. Specifically, as described below, the reflectance estimation network may be applied to the original brightness image 308 to obtain an inverse of illumination, the product of which with the original brightness equals the reflectance of the image. An exemplary relationship between brightness (V), illumination (I), the inverse of illumination (L), and reflectance (R) are provided below in expressions 2 and 3. Using the Retinex variant (inverse of illumination), information loss during reconstruction of the image may be minimized.

$$V = R \cdot I \quad (2)$$

$$R = V \cdot L \quad (3)$$

The reflectance estimation network 312 generates reflectance images for each of the disturbed brightness image 310 and the original brightness image 308. The disturbed brightness image may exhibit the same relationships in expressions 2 and 3 described above with respect to the original brightness image 310, except with a disturbed reflectance, disturbed illuminance, and disturbed inverse of illuminance (shown below in expressions 4 and 5).

$$V' = R' \cdot I' \quad (4)$$

$$R' = V' \cdot L' \quad (5)$$

Figure 7:
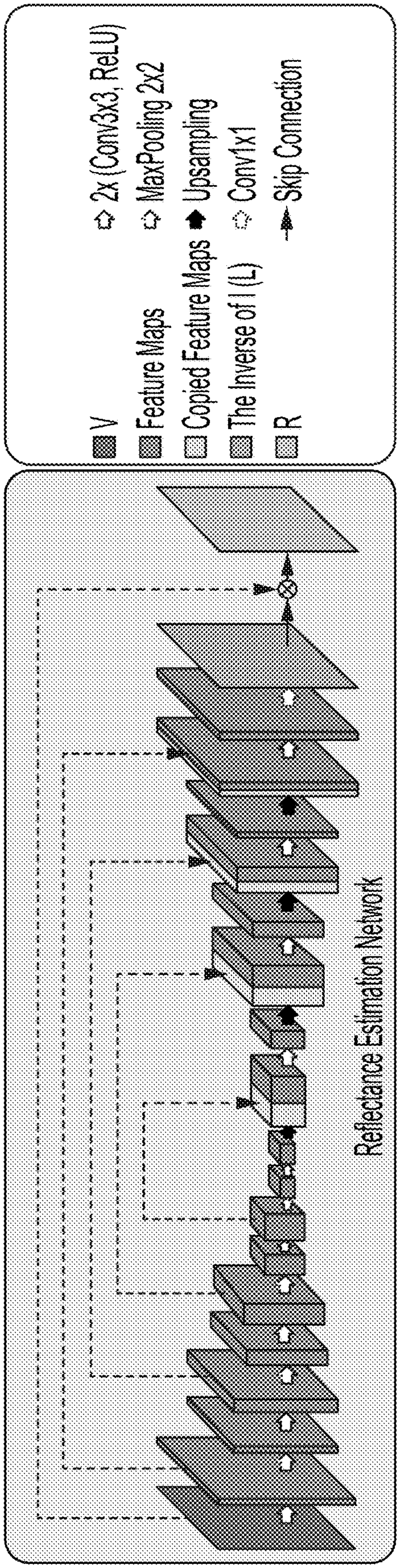
FIG. 7 is an example of a U-Net architecture that can be used for a reflectance estimation network.

The reflectance estimation network 312 may comprise a known U-Net architecture comprising a plurality of convolutional layers, downsampling steps, and upsampling steps. An example of a suitable U-Net architecture is illustrated in FIG. 7 and described in Jian, Z., et al., "A Switched View of Retinex: Deep Self-Regularized Low-Light Image Enhancement," Neurocomputing 454 (2021): 361-372, which is hereby incorporated by reference in its entirety. The exemplary U-Net architecture may comprise 19 convolutional layers, 4 downsampling steps, and 4 upsampling steps. In some examples, the architecture may comprise a different number of convolutional layers, downsampling steps, and/or upsampling steps. Each downsampling step may be a 2×2 max pooling operation with a stride of 2. Each upsampling step may be a bilinear interpolation that expands the height and width of the feature map to 2× the original. The network 312 may comprise 2 cascaded convolutional layers between 2 spatial resolution regulation operations. Each convolutional layer may comprise a 3×3 convolution operation with padding, followed by a rectified linear unit (ReLU) activation function. The reflectance estimation network 312 may not comprise batch normalization layers. The network 312 may comprise skip connections that concatenate feature maps of the downsampling process to the corresponding feature maps of the upsampling process based on space resolution, which may increase the amount of information in the upsampling steps. The reflectance image 314 and reflectance image 316 may be obtained as an element-wise product between the input (brightness image 308 and disturbed brightness image 310, respectively) and the inverse of illumination, as mentioned and illustrated in expressions 3 and 5 above.

The reflectance estimation network 312 may be self-regularized by various loss functions. Stated otherwise, the network 312 may not require a supervised learning process. For example, a set of functions may self-regularize the reflectance and the inverse of illumination, which may include a reflectance consistency loss function, an exposure control loss function, a spatial structure loss function, and an illumination smoothness loss function, each of which are described in greater detail below.

Based on Retinex theory, as mentioned above, the original brightness image 308 and disturbed brightness image 310 have substantially the same reflectance, and therefore, the fully trained reflectance estimation network should generate substantially the same reflectance image for both. The difference between the generated reflectance images during training, otherwise referred to as the reflectance consistency loss (Lrc), may be defined according to expression 6 provided below.

$$L_{rc}=\|R-R'\|_2^2 \tag{6}$$

The brightness of the generated reflectance image may be constrained by an exposure control loss function. The exposure control loss ($L_{ec}$) may measure the distance between the average brightness of a local region of generated reflectance and a predefined well-exposed value E. E denotes a normalized value of brightness of an optimally exposed region. Due to normalization, the range is between 0 and 1. The choice of the optimal value can be chosen empirically, such as via hyperparameter searching during training. An exemplary range of suitable values is 0.4 to 0.7. In some examples, E may be equal to 0.7. The exposure control loss function may be defined according to expression 7 below, where $R_n$ may denote the result of n×n average pooling of the generated reflectance (mentioned above) and E may denote a matrix equivalent in size to R. and may be pre-populated in each space of the matrix with the predefined value of E mentioned above (e.g., 0.7). Generally, n represents the size of non-overlapping local regions in the input image (squares of size n×n). The value for n may be chosen empirically, such as via hyperparameter searching during training, and can be chosen based at least in part on the input image resolution. In some examples, the value of n may influence the brightness and details of the image and thus may be predefined. For example, n may be equal to 16.

$$L_{ec}=\|R_n-E\|_2^2 \tag{7}$$

The spatial structure of the original input image may be reflected in the generated reflectance image using a spatial structure loss function. The spatial structure loss ($L_{ss}$) may determine the difference between the horizontal and vertical gradients of each pixel of the original input image and the generated reflectance image. The spatial structure loss may be defined according to expression 8 provided below. $R_m$ and $V_m$ may denote the result of m×m average pooling of the generated reflectance image and the input image, respectively. The value of m may be chosen empirically, such as via hyperparameter searching during training. In some examples, m may be equal to 4.

$$L_{ss}=\|\nabla R_m-\nabla V_m\|_2^2 \tag{8}$$

Total variation loss (TV) may be used to determine the smoothness loss, which may consider the gradient of adjacent pixels. Illumination smoothness loss ($L_{is}$) may be defined according to expression 9 provided below.

$$L_{is}=\|\nabla L\|_2^2+\|\nabla L'\|_2^2 \tag{9}$$

The total loss may consider each of the loss functions described above as well as the weight of illumination smoothness loss ($W_{is}$), provided below in expression 10. In some examples, the weight of illumination smoothness loss may be predetermined and equal to 10.

$$L=L_{rc}+L_{ec}+L_{ss}+W_{is}L_{is} \tag{10}$$

The loss function expressions described above are in accordance with an example training method for the reflectance estimation network 312. In some examples, one or more predetermined values described above may be different. In some examples, one or more of the above loss functions may be removed, and/or one or more additional loss functions may be added to the model.

The reflectance estimation network 312 illustrated in FIG. 3A may not require normal light images to train the network. Since training the reflectance estimation network 312 may not require a ground truth (because the network may be self-regularized), the reflectance estimation network 312 may be trained using under-exposed, over-exposed images, or a combination of under-exposed and over-exposed images, which can greatly expand the pool of training images that may be used.

Figure 3B:
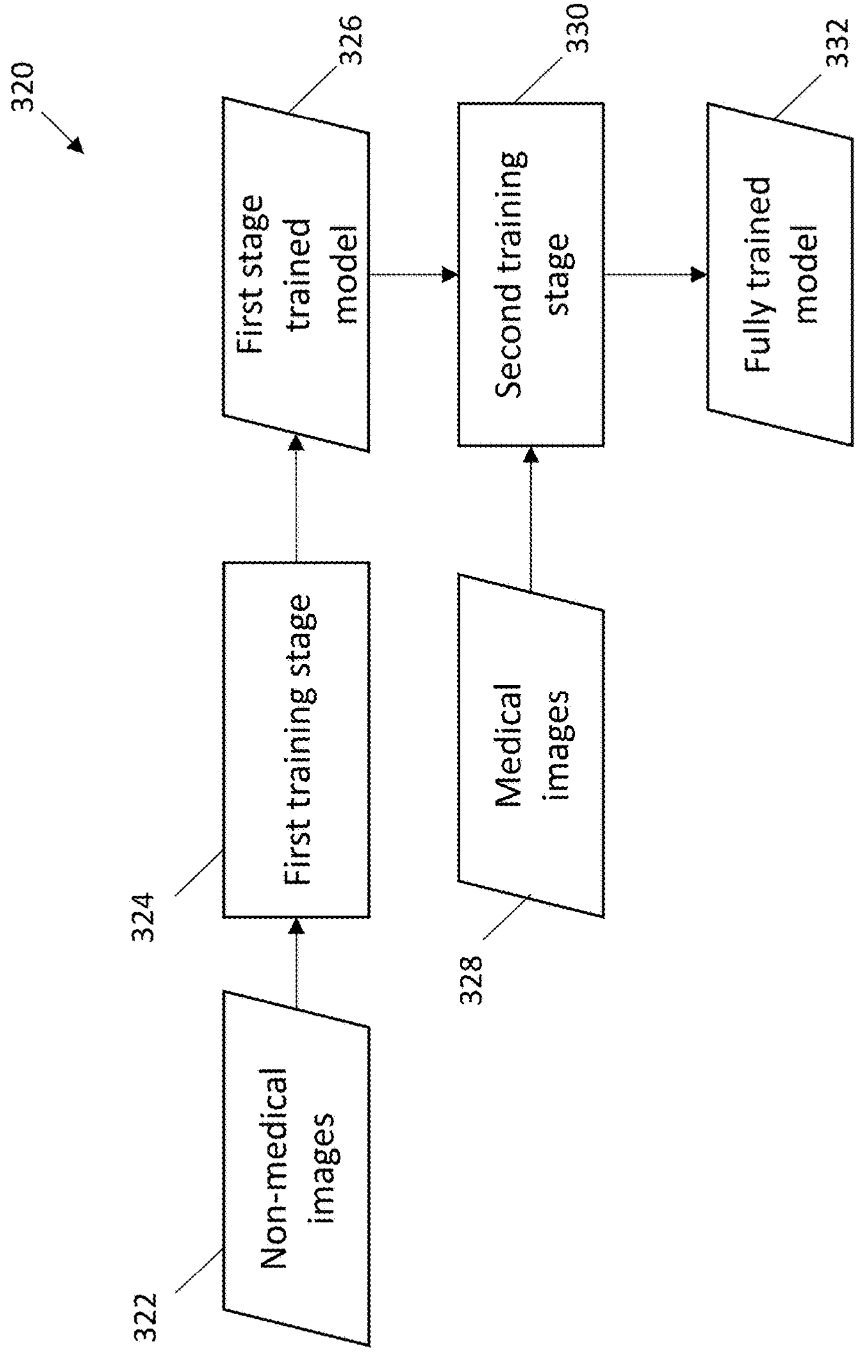
FIG. 3B illustrates an example method for training a machine learning model for generating a reflectance image using medical and non-medical images to train the machine learning model.

FIG. 3B illustrates an example method 320 for training a machine learning model with medical and non-medical images. As shown, the machine learning model may initially be trained at the first training stage 324 using non-medical images 322 to output a trained model 326. Non-medical images can include, for example, images of scenery, images of objects, and images of people. The first stage trained model 326 may undergo additional subsequent training with medical images 328 at second training stage 330 to output a fully trained model 332. Medical images 328 can include images corresponding to the images for which the machine learning model may be used. For example, medical images 328 can include endoscopic images for a machine learning model being trained for enhancing endoscopic images or open-field images for a machine learning model being trained for enhancing open-field images. Alternatively, any medical images may be used, regardless of their correspondence to the ultimate application of the machine learning model. Since non-medical images are, in general, more widely available, using non-medical images to train the machine learning model in a first stage and then using the medical images to refine the machine learning model can lead to easier and more robust training of the machine learning model. It is to be understood that first training stage 324 and second training stage 330 may comprise at least a portion of method 300 illustrated in FIG. 3A.

In some examples, the machine learning model may only require a single stage of training. In some examples, the machine learning model may be trained using more than two stages. The medical images used in training can be selected for training based on the type of imaging modality, the type of procedure, etc.

Figure 3C:
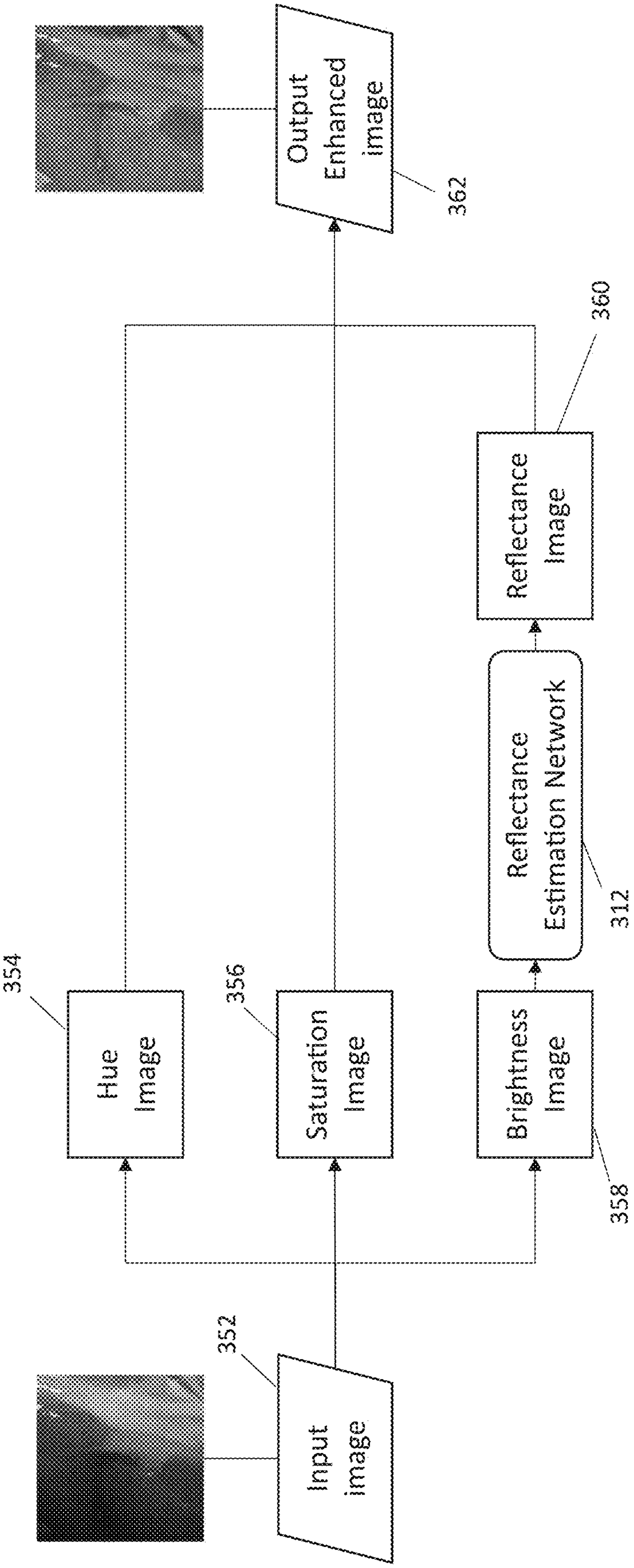
FIG. 3C illustrates an example of generating an enhanced image using a trained machine learning model.

FIG. 3C illustrates the use of the reflectance estimation network 312 in method 200 in a process for generating an enhanced image. An input image 352 is converted (e.g., from RGB color space) to a hue image 354 (the array of hue values resulting from the conversion), a saturation image 356 (the array of saturation values resulting from the conversion), and a brightness image 358 (the array of brightness values resulting from the conversion) according to step 204 of method 200. The brightness image 358 is fed to the reflectance estimation network 312 that has been trained according to method 300 to generate a reflectance image 360, which comprises an array of reflectance estimate values corresponding to the array of pixels of the input image 352. The reflectance estimation network can have been trained on medical images and/or non-medical images and in a single stage or in multiple stages, such as in the two stages shown in FIG. 3B. An output image 362 is generated by combining the reflectance image 360 with the hue image 354 and saturation image 356, such as by converting from HSB color space to RGB color space, where the reflectance image is used as the brightness component in the conversion.

Figure 4A:
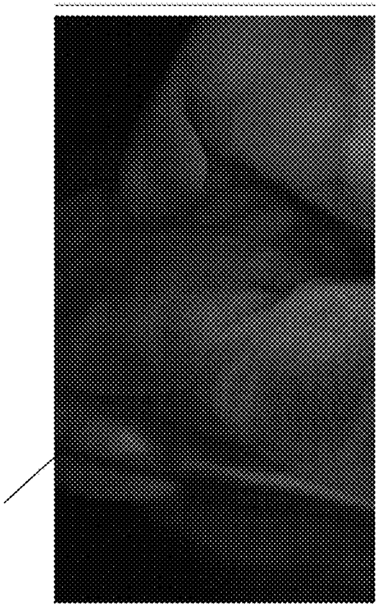
FIGS. 4A-4D illustrate example original and enhanced fluorescence medical images.
Figure 4B:
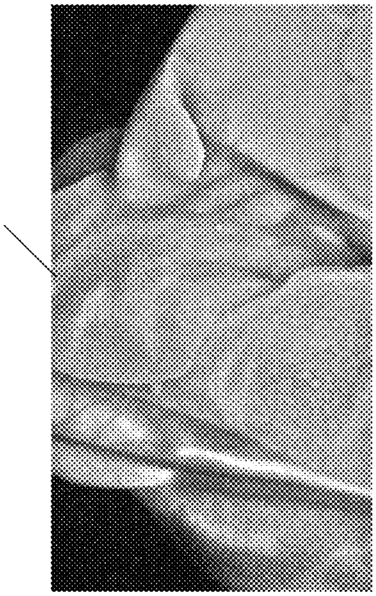
Figure 4C:
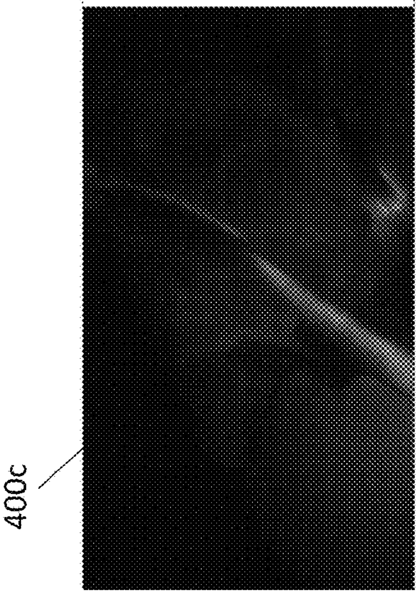
Figure 4D:
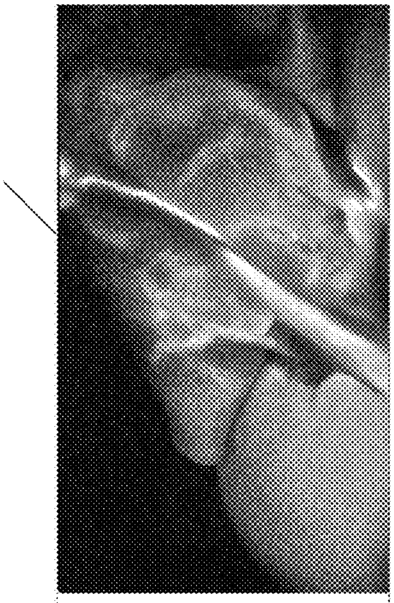

FIGS. 4A-4D and 5A-5D illustrate example original and enhanced medical images based on the various steps of method 200. FIGS. 4A and 4C illustrate original grayscale (e.g., fluorescence) images 400*a*, 400*c* that may be received as input by the image processing system, whereas FIGS. 4B and 4D illustrate enhanced fluorescence images 400*b*, 400*d* based on images 400*a*, 400*c* (respectively) and generated from the various steps of method 200. As shown, the enhanced images preserve the areas of each image that may comprise a higher brightness, while simultaneously revealing structure in dark areas that now appear uniformly lit.

Figures 5A, 5B, 5C, 5D:
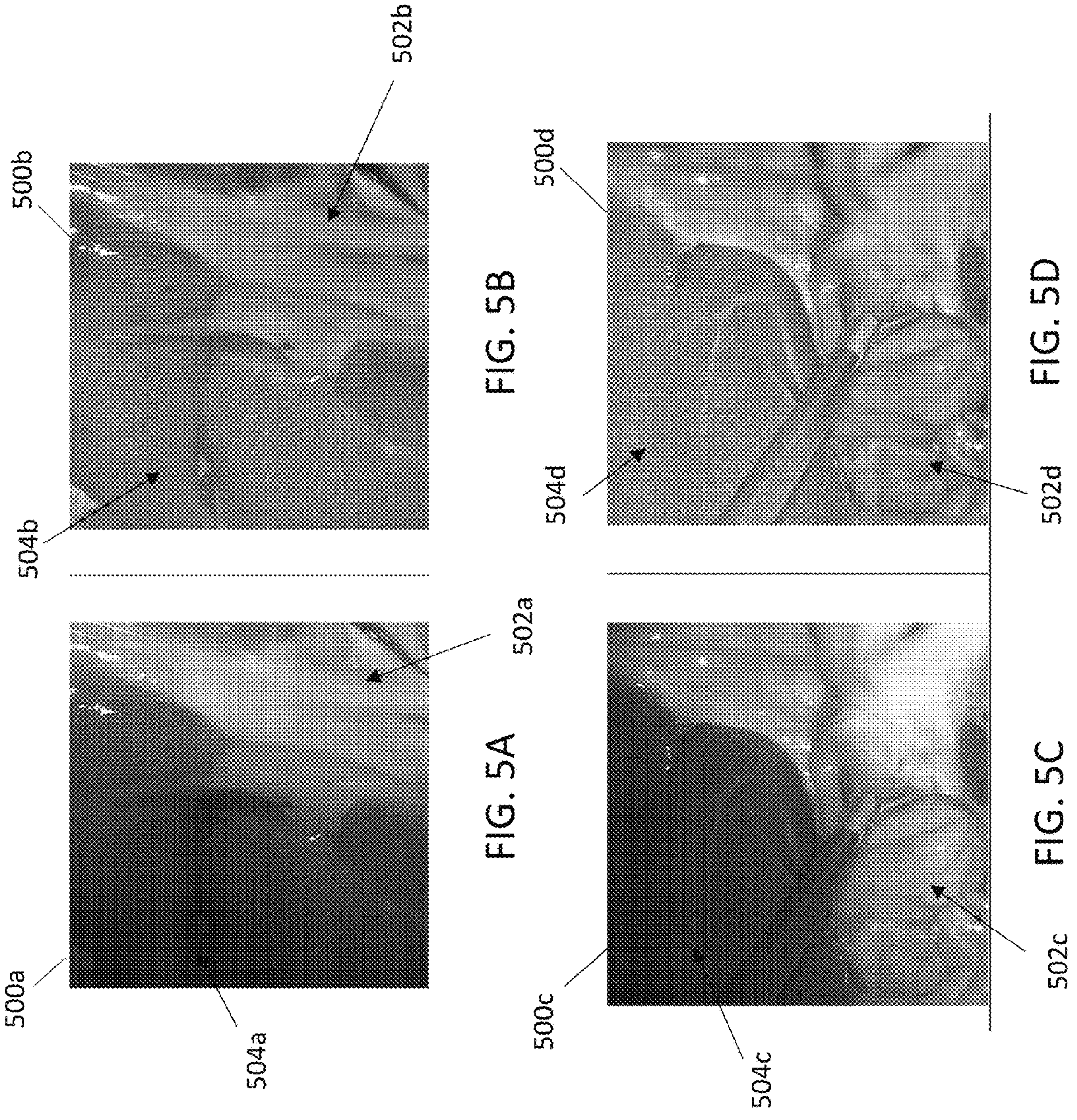
FIGS. 5A-5D illustrate example original and enhanced visible light medical images.

Likewise, FIGS. 5A and 5C illustrate original visible light images 500*a*, 500*c*, e.g. full color visible light images, that may be received as input by the image processing system, whereas FIGS. 5B and 5D illustrate enhanced visible light images 500*b*, 500*d* based on images 500*a*, 500*c* (respectively) and generated from the various steps of method 200. As shown, the enhanced images preserve the color of the well-lit areas, while simultaneously revealing the true color of the tissue that was previously not visible in the original images. For example, in FIG. 5A, the original image 500*a* comprises a light region 502*a* and a dark region 504*a*. After processing the image to generate the corresponding enhanced image 500*b* in FIG. 5B, it may be shown that the color and/or brightness of the light region 502*b* is substantially the same as that of light region 502*a* in image 500*a*, whereas the brightness of region 504*b* is improved in comparison to the corresponding region 504*a* of image 500*a*.

As noted above, the methods and systems described herein can be used on images received during the imaging session for displaying the enhanced images in real-time, such as for providing visual guidance during a surgical procedure. Alternatively, or additionally, the methods and systems may be applied to images after the imaging session. For example, as mentioned above, images may be received from a storage (e.g., memory), such as for post-operative review of the images, procedure summarization/reporting, and/or training purposes. The enhanced images can provide improved visualization of the imaged scene.

Enhanced images can be used to improve other downstream image processing tasks. For example, enhanced brightness images can be used as training data for training one or more machine learning models to perform one or more image analysis tasks, such as image segmentation and image classification. For example, the enhanced images may allow areas of interest (such as those comprising abnormalities) in the imaged tissue to be more efficiently identified and/or separated from the remainder of the image by a machine learning model. Additionally, the enhanced images may be easier for a user to manually label for generating labeled training data for training one or more machine learning models. Thus, image enhancement according to the principles described herein can increase the training data available to train machine learning models to perform image analysis tasks, which can decrease training time, increase model performance, and/or decrease training cost.

Because the color channels of the original medical image are preserved during image processing, color fidelity may be preserved. Thus, the enhanced medical images may improve the ability to identify abnormalities in the imaged tissue that may be reliant on data related to color (e.g., detection of pre-cancer lesions). For example, a user (or automated algorithm) may identify and label anatomy of interest in an enhanced medical image, which may be analyzed, stored, and/or applied as training data for other machine learning models. Thus, the accuracy of machine learning models that use enhanced medical images (whether labeled or unlabeled) as training data may be improved.

Figure 6:
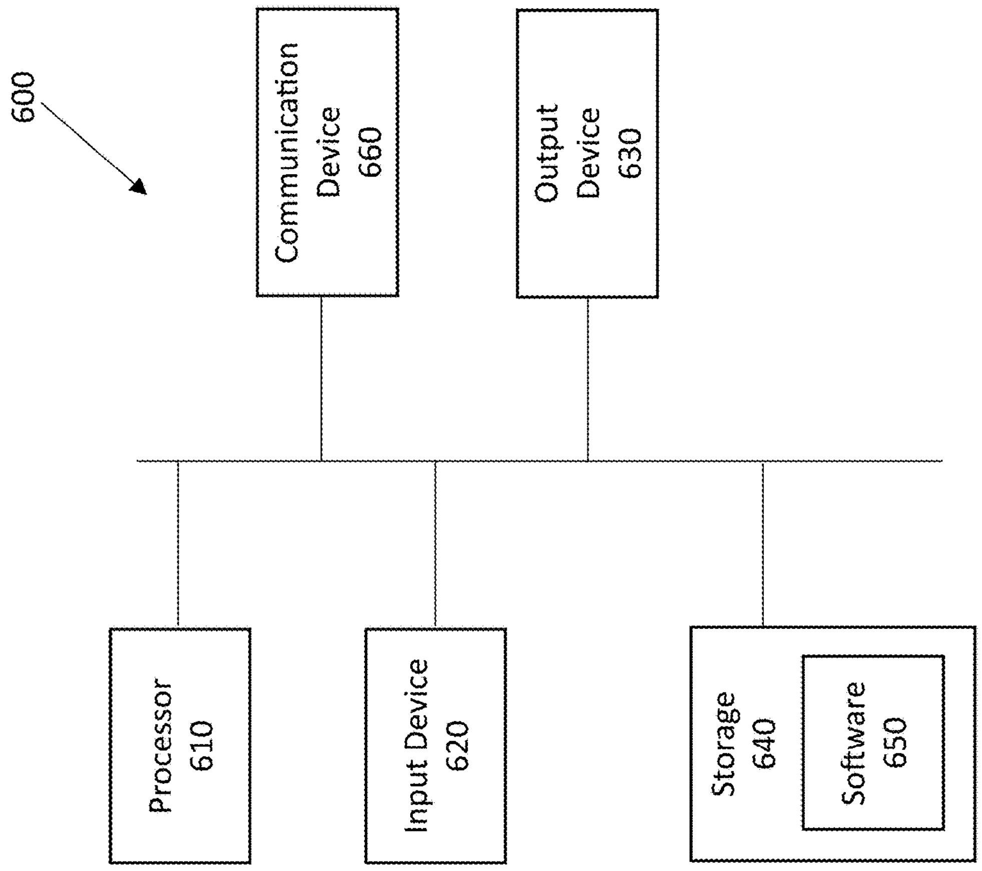
FIG. 6 illustrates an example computing system.

FIG. 6 illustrates an example of a computing system 600 that can be used for one or more of components of system 100 of FIG. 1, such as one or more of image acquisition assembly 104, light source 108, camera control unit 120, and image processing unit 122. System 600 can be a computer connected to a network, such as one or more networks of hospital, including a local area network within a room of a medical facility and a network linking different portions of the medical facility. System 600 can be a client or a server. As shown in FIG. 6, system 600 can be any suitable type of processor-based system, such as a personal computer, workstation, server, handheld computing device (portable electronic device) such as a phone or tablet, or dedicated device. The system 600 can include, for example, one or more of input device 620, output device 630, one or more processors 610, storage 640, and communication device 660. Input device 620 and output device 630 can generally correspond to those described above and can either be connectable or integrated with the computer.

Input device 620 can be any suitable device that provides input, such as a touch screen, keyboard or keypad, mouse, gesture recognition component of a virtual/augmented reality system, or voice-recognition device. Output device 630 can be or include any suitable device that provides output, such as a display, touch screen, haptics device, virtual/augmented reality display, or speaker.

Storage 640 can be any suitable device that provides storage, such as an electrical, magnetic, or optical memory including a RAM, cache, hard drive, removable storage disk, or other non-transitory computer readable medium. Communication device 660 can include any suitable device capable of transmitting and receiving signals over a network, such as a network interface chip or device. The components of the computing system 600 can be connected in any suitable manner, such as via a physical bus or wirelessly.

Processor(s) 610 can be any suitable processor or combination of processors, including any of, or any combination of, a central processing unit (CPU), graphics processing unit (GPU), field programmable gate array (FPGA), and application-specific integrated circuit (ASIC). Software 650, which can be stored in storage 640 and executed by one or more processors 610, can include, for example, the programming that embodies the functionality or portions of the functionality of the present disclosure (e.g., as embodied in the devices as described above). For example, software 650 can include one or more programs for execution by one or more processor(s) 610 for performing one or more of the steps of method 200.

Software 650 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 600 can implement any operating system suitable for operating on the network. Software 650 can be written in any suitable programming language, such as C, C++, Java, or Python. In various examples, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method of enhancing medical images comprising, at a computing system:

receiving a medical image;

converting the medical image into a brightness component image and two color component images;

generating a reflectance image from the brightness component image using a machine learning model, wherein the reflectance image comprises a plurality of reflectance estimates, each reflectance estimate being an estimate of a ratio of light reflected from a surface to a total amount of light incident on the surface; and generating an enhanced medical image based on the reflectance image and the two color component images.

2. The method of claim 1, wherein the enhanced medical image comprises at least one region that is brighter than a corresponding region of the medical image.

3. The method of claim 1, wherein the machine learning model was trained on training images that comprise non-medical training images.

4. The method of claim 3, wherein the machine learning model was trained on the non-medical training images in a first training stage and trained on medical training images in a second training stage that is subsequent to the first training stage.

5. The method of claim 1, wherein generating the enhanced medical image comprises applying at least one de-noising algorithm.

6. The method of claim 1, wherein the medical image comprises a grayscale image.

7. The method of claim 6, wherein the grayscale image comprises three color components.

8. The method of claim 1, wherein the two color component images are a hue image and a saturation image.

9. The method of claim 1, wherein the medical image is a fluorescence image and the enhanced medical image comprises a combination of a visible light image with the reflectance image.

10. The method of claim 1, wherein the medical image comprises a fluorescence image and the enhanced medical image comprises an enhanced fluorescence image.

11. The method of claim 10, comprising receiving a visible light image and combining the visible light image with the enhanced fluorescence image.

12. The method of claim 1, comprising displaying the enhanced medical image during a medical procedure.

13. The method of claim 1, comprising generating a medical procedure report that comprises the enhanced medical image.

14. The method of claim 1, comprising:

displaying the enhanced medical image to a user;

receiving at least one input from the user for labeling anatomy of interest in the medical image to generate a training medical image; and training a different machine learning model to identify the anatomy of interest based on the training medical image.

15. The method of claim 1, wherein the medical image is one of a plurality of medical images captured under multiple lighting conditions, and the method comprises:

generating a plurality of enhanced medical images from the plurality of medical images using the machine learning model; and training a different machine learning model based on the plurality of enhanced medical images.

16. The method of claim 1, wherein the medical image comprises a video frame.

17. The method of claim 1, wherein the medical image comprises an endoscopic image.

18. The method of claim 1, wherein the medical image comprises an open-field image.

19. The method of claim 1, comprising receiving a user input selecting an enhancement mode, and generating the enhanced medical image in response to receiving the user input.

20. A computing system comprising one or more processors, memory, and one or more programs stored in the memory for execution by the one or more processors, the one or more programs including instructions that, when executed by the one or more processors, cause the computing system to:

receive a medical image;

convert the medical image into a brightness component image and two color component images;

generate a reflectance image from the brightness component image using a machine learning model, wherein the reflectance image comprises a plurality of reflectance estimates, each reflectance estimate being an estimate of a ratio of light reflected from a surface to a total amount of light incident on the surface; and generate an enhanced medical image based on the reflectance image and the two color component images.

21. The system of claim 20, wherein the enhanced medical image comprises at least one region that is brighter than a corresponding region of the medical image.

22. The system of claim 20, wherein the machine learning model was trained on training images that comprise non-medical training images.

23. The system of claim 22, wherein the machine learning model was trained on the non-medical training images in a first training stage and trained on medical training images in a second training stage that is subsequent to the first training stage.

24. The system of claim 20, wherein generating the enhanced medical image comprises applying at least one de-noising algorithm.

25. The system of claim 20, wherein the medical image comprises a grayscale image.

26. The system of claim 25, wherein the grayscale image comprises three color components.

27. The system of claim 20, wherein the two color component images are a hue image and a saturation image.

28. The system of claim 20, wherein the medical image is a fluorescence image and the enhanced medical image comprises a combination of a visible light image with the reflectance image.

29. The system of claim 20, wherein the medical image comprises a fluorescence image and the enhanced medical image comprises an enhanced fluorescence image.

30. The system of claim 29, wherein the one or more programs include instructions for receiving a visible light image and combining the visible light image with the enhanced fluorescence image.

31. The system of claim 20, wherein the one or more programs include instructions for displaying the enhanced medical image during a medical procedure.

32. The system of claim 20, wherein the one or more programs include instructions for:

displaying the enhanced medical image to a user;

receiving at least one input from the user for labeling anatomy of interest in the medical image to generate a training medical image; and training a different machine learning model to identify the anatomy of interest based on the training medical image.

33. The system of claim 20, wherein the medical image is one of a plurality of medical images captured under multiple lighting conditions, wherein the one or more programs include instructions for:

generating a plurality of enhanced medical images from the plurality of medical images using the machine learning model; and training a different machine learning model based on the plurality of enhanced medical images.

34. The system of claim 20, wherein the one or more programs include instructions for receiving a user input selecting an enhancement mode, and generating the enhanced medical image in response to receiving the user input.

* * * * *